(12) United States Patent
    Griffin

(10) Patent No.: US 9,031,249 B1
(45) Date of Patent: May 12, 2015

(54) ELECTROLARYNX

(71) Applicant: Clifford Jay Griffin, Murrieta, CA (US)

(72) Inventor: Clifford Jay Griffin, Murrieta, CA (US)

( * ) Notice: Subject to any disclaimer, the term of this patent is extended or adjusted under 35 U.S.C. 154(b) by 451 days.

(21) Appl. No.: 13/663,892

(22) Filed: Oct. 30, 2012

(51) Int. Cl.
    *A61F 2/20* (2006.01)
(52) U.S. Cl.
    CPC ............. *A61F 2/20* (2013.01); *A61F 2002/206* (2013.01)
(58) Field of Classification Search
    CPC .............................. A61F 2/20; A61F 2002/206
    USPC ............................................................. 381/70
    See application file for complete search history.

(56) References Cited

U.S. PATENT DOCUMENTS

| | | | |
|---|---|---|---|
| 6,252,966 B1 * | 6/2001 | Griffin | 381/70 |
| 7,212,639 B1 * | 5/2007 | Houston | 381/70 |
| 2003/0031326 A1 * | 2/2003 | Lukacovic | 381/70 |
| 2014/0079233 A1 * | 3/2014 | Kamradt et al. | 381/70 |

* cited by examiner

*Primary Examiner* — Sonia Gay
(74) *Attorney, Agent, or Firm* — Loyal McKinley Hanson

(57) ABSTRACT

An electrolarynx includes a cylindrically shaped handheld case having an inner wall that defines a hollow interior. A circuit board within a mid portion of the hollow interior drives a sound-producing transducer component within a distal end portion. Two wires electrically connect the circuit board to the transducer component. First and second wire-guiding structures are provided that have been integrally molded with the rest of the case at diametrically opposite locations along the inner wall of the distal end portion, where they maintain bends in the two wires from longitudinally extending wire paths coming from the circuit board to circumferentially extending wire paths going to wire attachment points on the transducer, thereby facilitating fabrication while avoiding wire interference with transducer operation.

13 Claims, 7 Drawing Sheets

ELECTROLARYNX

BACKGROUND OF THE INVENTION

1. Technical Field

This invention relates generally to electromechanical speech aids commonly referred to as artificial larynxes and electrolarynxes, and more particularly to an improved electrolarynx construction that significantly reduces fabrication time and expense while improving operational aspects.

2. Description of Related Art

Persons without normal use of their vocal cords or larynx often use an electrolarynx to speak. The electrolarynx includes a sound-producing transducer that delivers an electrolarynx tone having a fundamental frequency in the speech range of the average human voice. To speak, the user introduces this artificially generated tone into a resonant speech cavity (i.e., the mouth, nose, or pharynx). While doing so, the user modulates the electrolarynx tone by varying the shape of the resonant speech cavity and by making the usual tongue, teeth, and lip constrictions so as to articulate the modulated tone as human speech.

U.S. Pat. Nos. 5,812,681 and 6,252,966 issued to Clifford J. Griffin describe some existing electrolarynxes. Similar in some respects to other existing artificial larynxes, each of the Griffin electrolarynxes includes a four-inch to five-inch long cylindrically shaped case that houses a electronic circuit board, a battery, an electro-mechanical transducer for producing vibrations (i.e., the tone), a volume control, and an ON-OFF switch. The user grasps the case, actuates the ON-OFF switch and volume control, and then presses the transducer portion of the electrolarynx against the outside of their throat so that vibrations travel through the throat tissues and into the mouth and throat. By varying pressure on the pushbutton switch of one model, the user varies the frequency of the tone to produce a more readily comprehensible voice.

One concern common to manufacturers of such electrolarynxes is fabrication cost. Assembling all the components in the cylindrical (or other shape) case can be a time consuming, high skill, and expensive task. Moreover, inadequate fabrication techniques can adversely affect performance. So, manufacturers seek improved techniques for facilitating fabrication.

Consider, for example, the task of connecting two wires from the circuit board to the sound-producing transducer. After mounting the circuit board in a mid portion of the hollow case, an assembler routes two wires from the circuit board to a hollow distal end portion of the case in which the transducer is located. The assembler routes the two wires longitudinally from the circuit board to the distal end portion. Next, from the inner wall of the distal end portion, the assembler routes the two wires circumferentially and radially inward toward two attachment points on an upper surface of the transducer housing. Then, the assembler glues or otherwise attaches terminal ends of the wires to the transducer housing at the two attachment points. The assembler may temporarily secure the wires in place with small alligator clips as glue dries to hold the wires to the attachment points, and after waiting for the glue to dry, remove the alligator clips and proceed with the rest of the assembly procedure.

One major concern of the foregoing is that assembly requires considerable skill and time. In addition, wire improper wire placement can adversely affect transducer operation. Thus, manufacturers need an electrolarynx with fabrication facilitating features that better reduce fabrication costs and insured desired electrolarynx performance.

SUMMARY OF THE INVENTION

In view of the foregoing, it is a primary object of the present invention to provide an electrolarynx that alleviates the concerns outlined above. The present invention achieves this objective by providing wire-guiding structures integrally molded with the rest of the electrolarynx case that facilitate the wiring task by holding the wires in desired orientations as fabrication proceeds. Moreover, the wire guides secure the wires in the desired orientations in order to preserve transducer performance.

To paraphrase some of the more precise language appearing in the claims and further introduce the nomenclature used, an electrolarynx constructed according to the invention includes a cylindrically shaped handheld case having an inner wall that defines a hollow interior. A circuit board within a mid portion of the hollow interior drives a sound-producing transducer component within a distal end portion. Two wires electrically connect the circuit board to the transducer component. First and second wire-guiding structures are provided that have been integrally molded with the rest of the case in the distal end portion along the inner wall at diametrically opposite locations, where they maintain bends in the two wires from longitudinally extending wire paths coming from the circuit board to circumferentially extending wire paths going to wire attachment points on the transducer, thereby facilitating fabrication while avoiding wire interference with transducer operation.

The first and second wires are thereby routed in a balanced way that facilitates fabrication while avoiding wire interference with operation of the transducer component. The following illustrative drawings and detailed description make the foregoing and other objects, features, and advantages of the invention more apparent.

DESCRIPTION OF THE PREFERRED EMBODIMENTS

Figure 1:
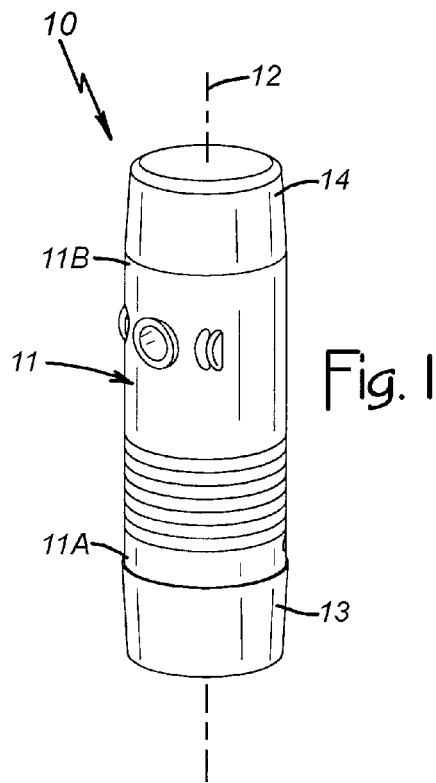
FIG. 1 of the drawings is a perspective view of an electrolarynx constructed according to the invention.
Figure 6:
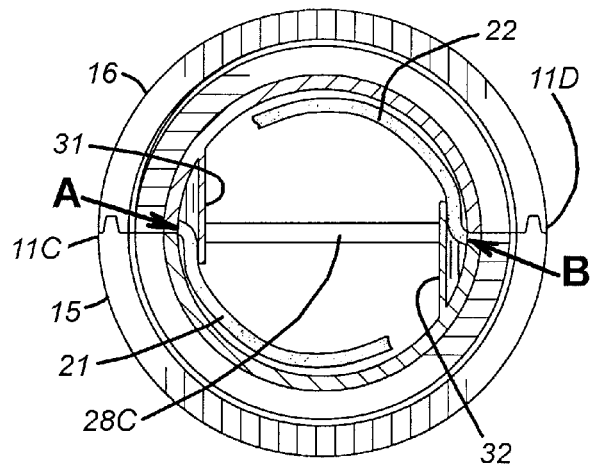
FIG. 6 is a cross section of the distal end portion of the case as viewed in a plane containing a line 6-6 in FIG. 2, with the transducer component omitted.
Figure 5:
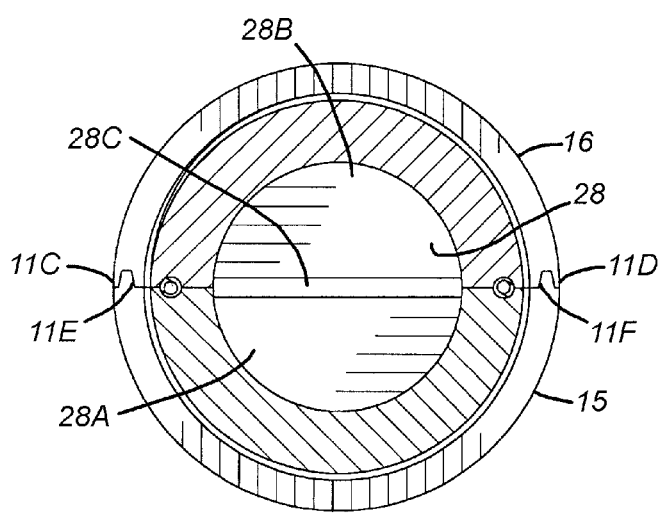
FIG. 5 is a cross section of the distal end portion of the case as viewed in a plane containing a line 5-5 in FIG. 2, with the transducer component omitted for illustrative purposes.

FIG. 1 of the drawings shows an electrolarynx 10 constructed according to the invention. The general structure of the electrolarynx 10 is considered first as background for the fabrication facilitating features. Generally, the electrolarynx 10 includes a case 11 that extends along a central axis of elongation 12 of the case 11, between a first or bottom end cap 13 at a rearward end 11A of the case and a second or top end cap 14 at a forward end 11B of the case. The user grasps the case 11, presses the top end cap 14 (i.e., the sound-producing transducer portion at the forward end of the electrolarynx 10) against the outside of their throat in order to introduce the electrolarynx tone to their mouth and throat, and then modulates that tone by varying the shape of the resonant speech cavity and by making the usual tongue, teeth, and lip constrictions so as to articulate the modulated tone as human speech.

Figure 2:
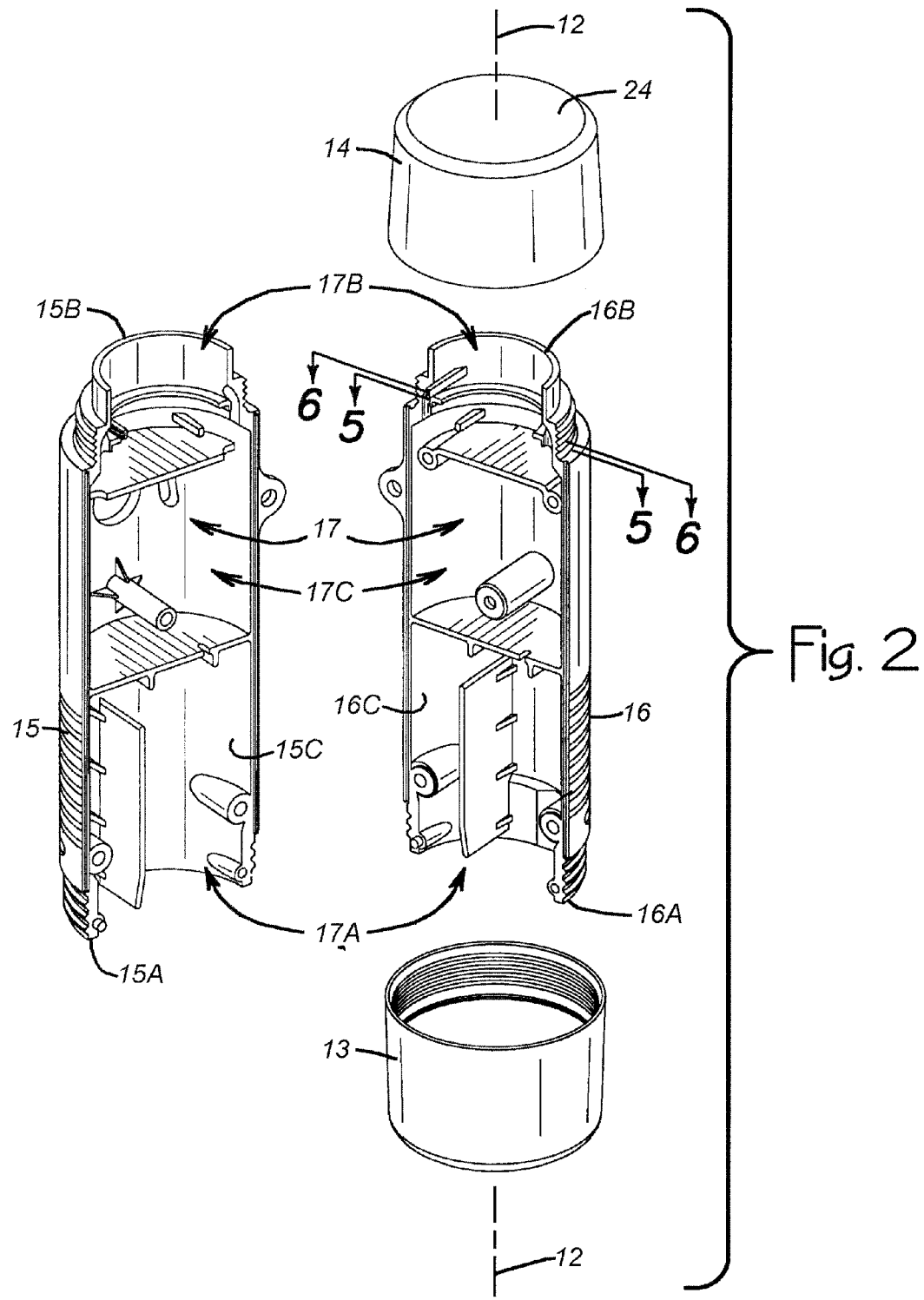
FIG. 2 of the drawings is an exploded view of the electrolarynx case and two end caps.

FIG. 2 is an exploded view of the electrolarynx 10 that shows further details of the case 11. The case 11 is a handheld molded-plastic component having an overall length of about 4.6 inches measured along the central axis of elongation 12. Of course, that dimension provides an idea of the size of the various components of the illustrated embodiment; it is not critical to the present invention. The case 11 includes a first section or half 15 and a second section or half 16 that, when fully assembled, are held together by the bottom and top end caps 13 and 14. The assembler person screws the bottom and top end caps 13 and 14 onto the first and second sections 15 and 16, in threaded engagement of the first and second sections 15 and 16.

The first half 15 of the case 11 has a bottom end 15A, a top end 15B and an inner wall 15C extending between the bottom and top ends 15A and 15B. Similarly, the second half 16 has a bottom end 16A, a top end 16B, and an inner wall 16C extending between the bottom and top ends 16A and 16B. When the first and second halves 15 and 16 are fully assembled, the inner walls 15C and 16C of the first and second halves 15 and 16 combine as an inner wall 15C-16C (i.e., the combination of 15C and 16C) that defines a hollow interior 17 of the case 11, a hollow interior centered on the central axis of elongation 12 that houses various electronic components of the electrolarynx 10. With the first and second sections 15 and 16 fully assembled, the hollow interior 17 extends along the central axis of elongation 12 of the case 11, from a proximal end portion 17A of the hollow interior 17 (or rearward end portion) at the rearward end 11A of the case 11 to a distal end portion 17B of the hollow interior 17 (or forward end portion) at a forward end 11B of the case 11, and it includes a mid portion 17 C that provides a space for a circuit board.

Figure 3:
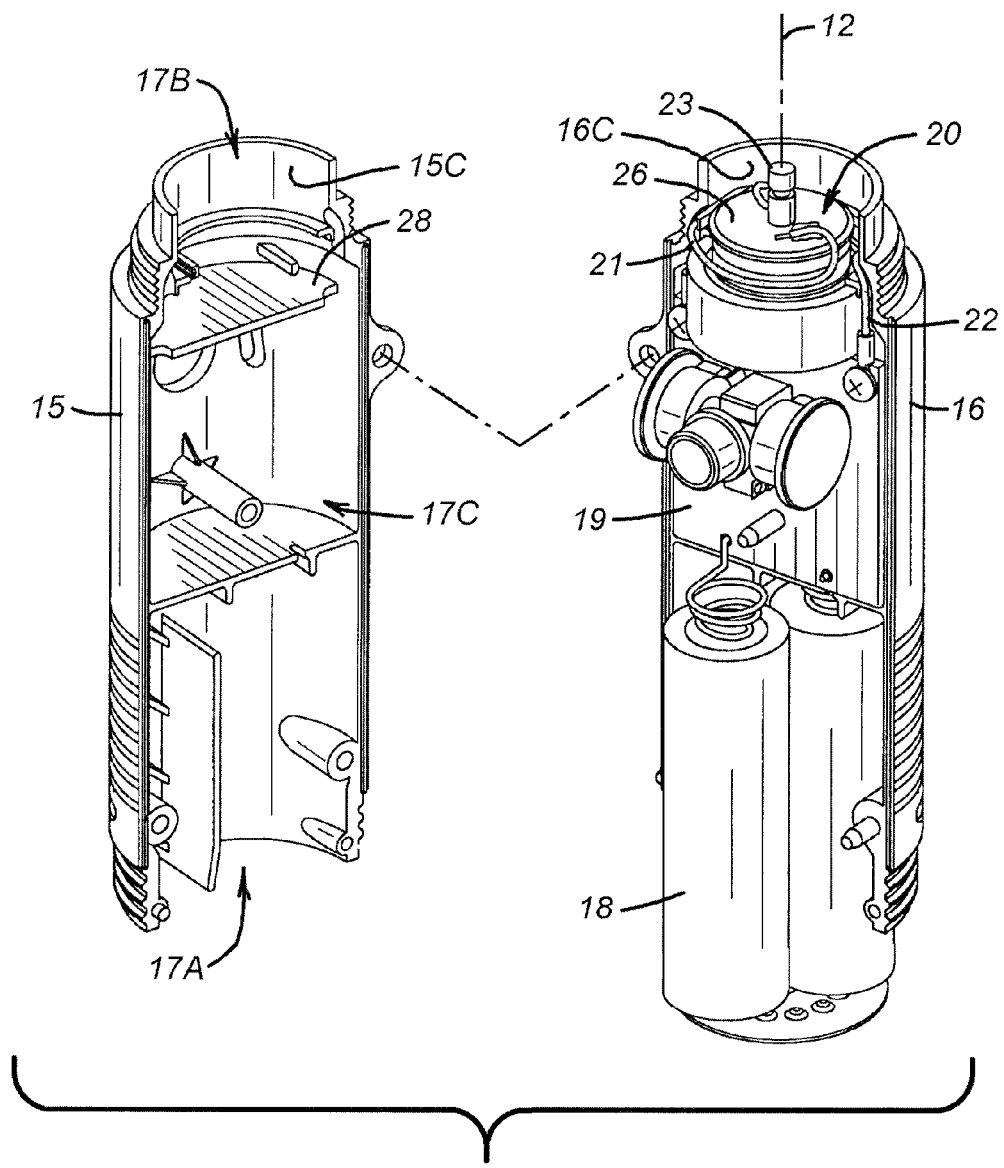
FIG. 3 is an exploded view of the case after electronic components have been assembled within the case.

Some electronic components of the electrolarynx 10 have been added to the second half 16 of the case 11 in the exploded view of FIG. 3, including a battery power supply 18 in the proximal end portion 17A of the hollow interior 17, a circuit board 19 in the mid portion 17C, and a transducer component 20 in the distal end portion 17B. A first wire 21 and a second wire 22 (e.g., insulated 24-gauge stranded wire) electrically connect the circuit board 19 to the transducer component 20. The transducer component 20, also referred to as an electromechanical transducer assembly, is a known type of component that includes a coil of 38-gauge magnet wire (described later on with reference to FIG. 8) for producing a magnetic field that causes a plunger 23 aligned with the central axis of elongation 12 to vibrate against a button-like diaphragm 24 (FIG. 2), thereby to produce a buzzing electrolarynx sound. The two wires 21 and 22 connect the circuit board 19 to the free ends of the magnet wire. They must do so carefully in a balanced and non-obtrusive way in order to preserve high-quality sound properties of the transducer component 20 and thereby of the electrolarynx 10, and it is the assembly of these two wires 21 and 22 that the present invention facilitates.

Figure 4:
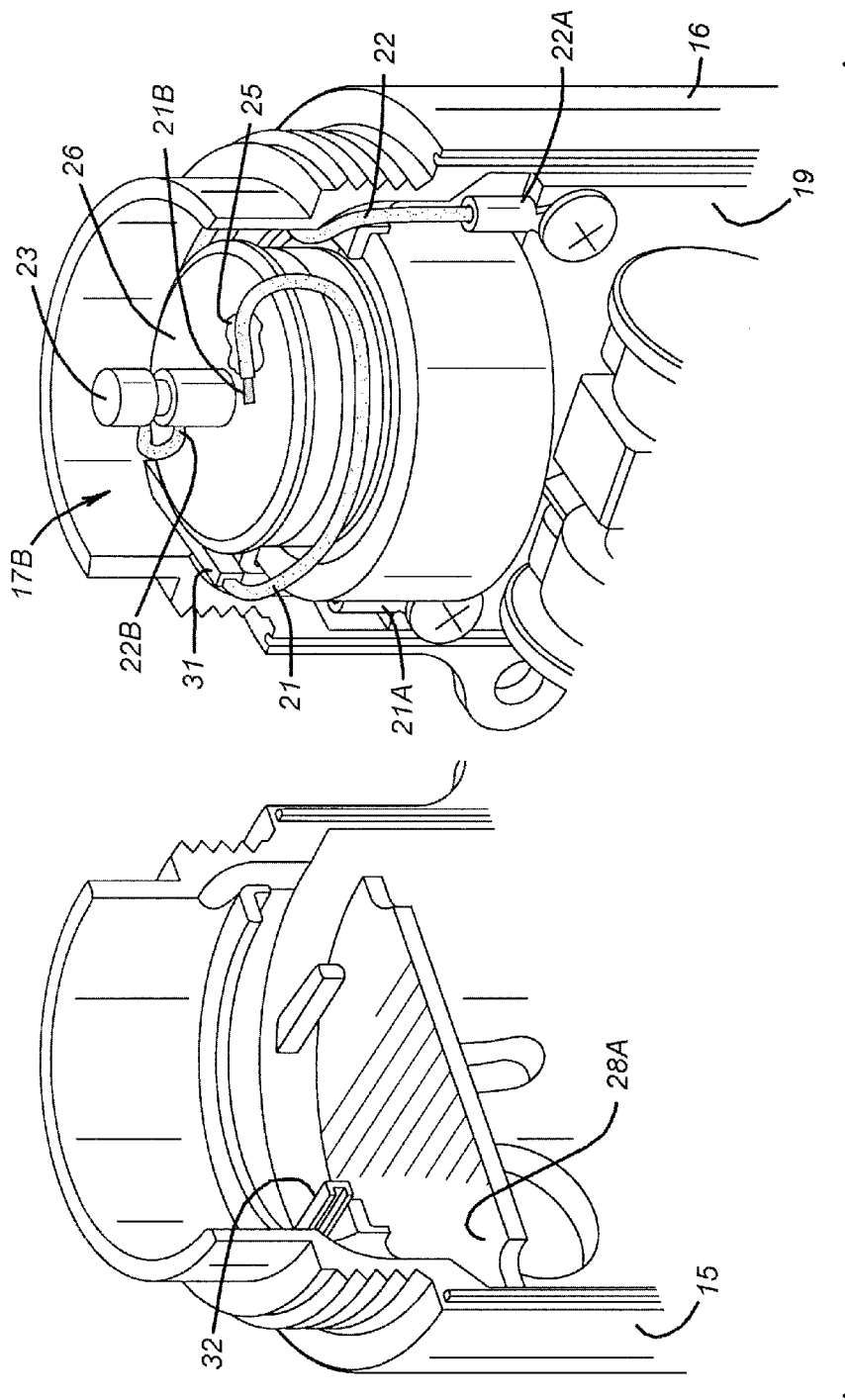
FIG. 4 is an enlarged exploded view of the distal end portion of the case.
Figure 7:
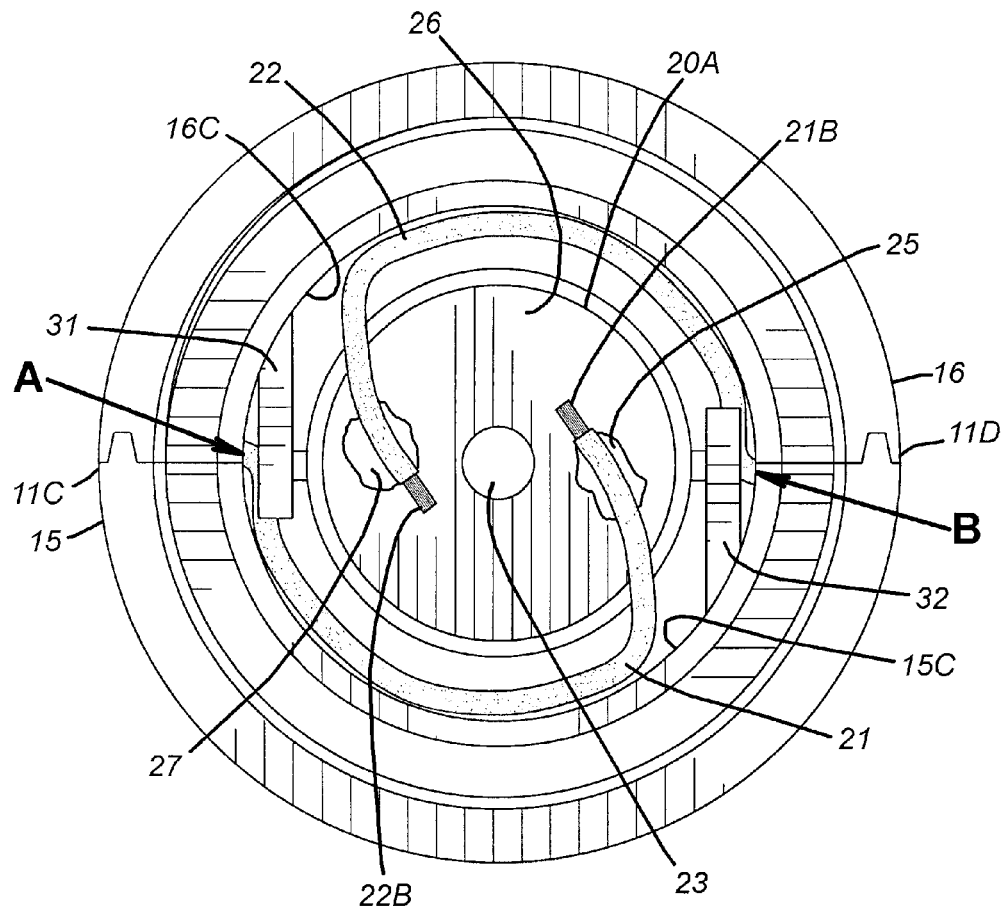
FIG. 7 is an enlarged top view of the case showing the wires routed to attachment points on the transducer component.
Figure 8:
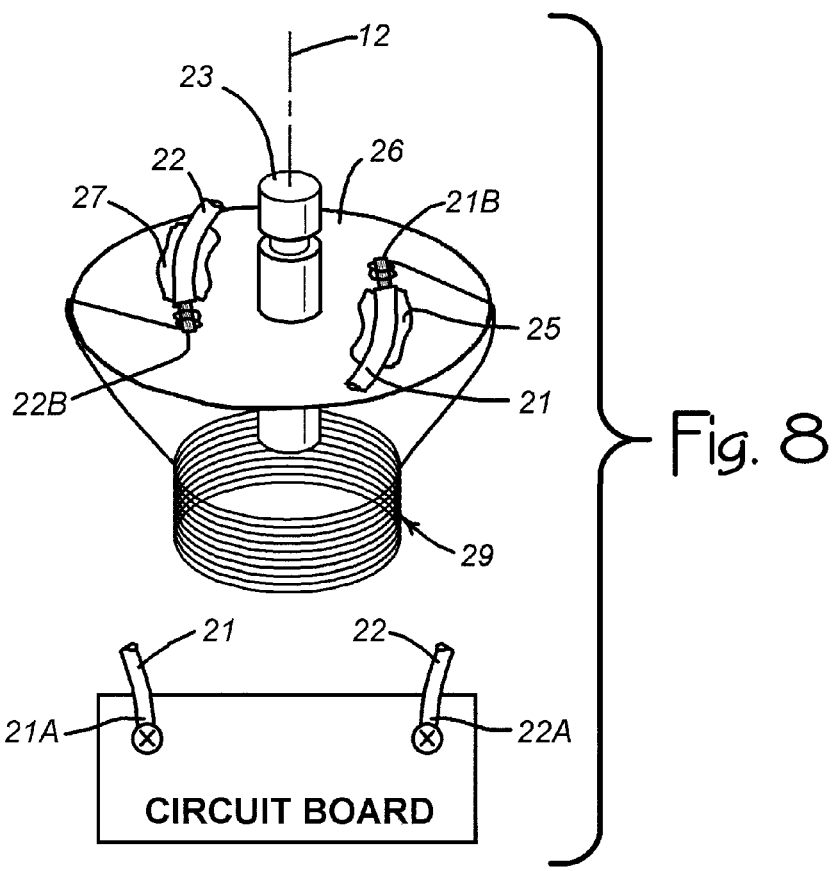
FIG. 8 is a diagrammatic view of the electrical connections of the coil in the transducer component to the two wires leading to the circuit board.
Figure 9:
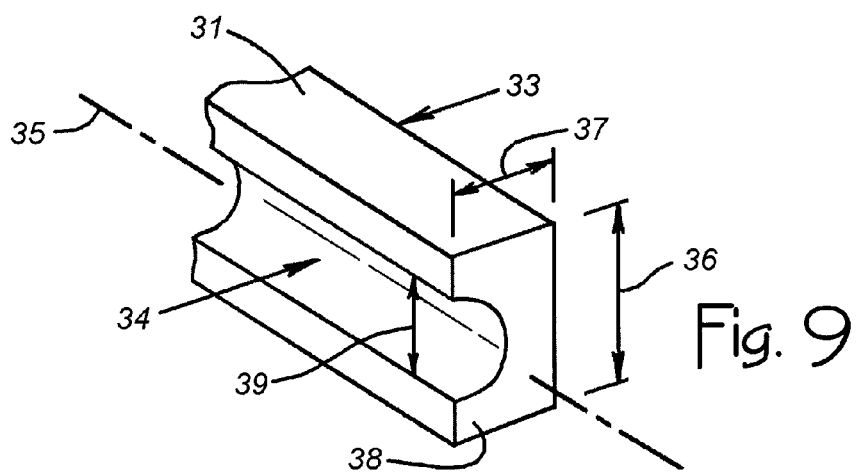
FIG. 9 is an enlarged diagrammatic perspective view of a portion of the first wire guide.
Figure 10:
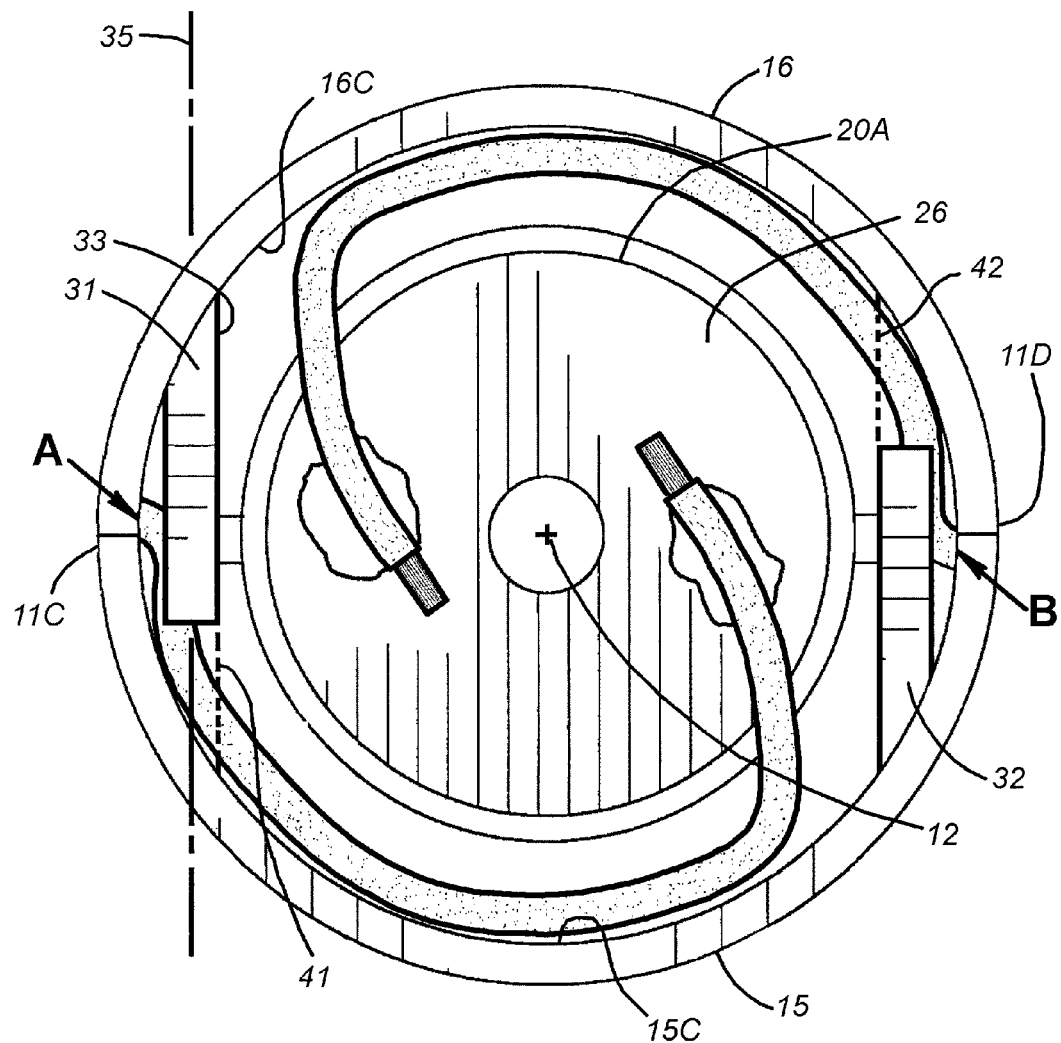
FIG. 10 is an enlarged top view of the distal end portion showing further details of wire guide placement.

FIGS. 4 through 10 show additional details related to wire routing. First consider FIG. 4. It is an enlarged exploded view of the forward end portion of the case 11 showing the transducer component 20 within the distal end portion 17B of the hollow interior 17. The first wire 21 has a first end portion 21A that is connected to the circuit board 19 by a solder lug or other suitable means (FIGS. 4 and 9), and a second end portion 21B that is glued or otherwise physically attached at a first attachment point 25 to an upper surface 26 of a cylindrically shaped, 0.660-inch outside diameter, housing 20A portion of the transducer component 20 (FIGS. 4, 7, and 8). Similarly, the second wire 22 has a first end portion 22A that is connected to the circuit board 19 (FIGS. 4 and 8), a second end portion 22B that is glued or otherwise physically attached at a second attachment point 27 to the upper surface 26 (FIGS. 7 and 8). Glue is depicted on the surface 26 at the first and second attachment points 25 and 27 in FIGS. 3, 4, 7, 8 and 10 of the drawings.

The upper surface 26 of the transducer housing 20A lies in a plane that is perpendicular to the axis of elongation 12 of the case 11 and parallel to a transducer-supporting surface 28 (FIGS. 3 and 5) that separates the mid portion 17C of the hollow interior 17 from the distal end portion 17B. The transducer-supporting surface 28 in FIG. 5 includes a first portion 28A that is part of the first section 15 of the case 11, and a second portion 28B that is part of the second section 16 of the case 11. A space 28C between those two portions (FIGS. 5 and 6) provides an opening through which the first and second wires 21 and 22 pass as they extend to respective ones of a first location A and second location B (FIGS. 6 and 7) in the distal end portion 17B of the hollow interior 17.

The first location A (FIGS. 6, 7, and 10) is located along the inner wall 16C at the forward end of the case 11, at approximately the level of the upper surface 26 of the transducer component 20 and at or near a first joint between the first and second sections 15 and 16 on a first side 11C of the case 11. The first location A and the upper surface 26 of the transducer housing 20A are both at a common distance, approximately, from a plane containing the transducer-supporting surface 28 mentioned previously. The second location B (FIGS. 6, 7, and 10) is located diametrically opposite the first location A, along the inner wall 15C at the forward end of the case 11, at approximately the level of the upper surface 26 and at or near a second joint between the first and second sections 15 and 16 on a diametrically opposite second side 11D of the case 11. The first and second joints are identified in FIG. 5 as first and second joints 11E and 11F.

The first and second locations A and B are transition points where the two wires 21 and 22 bend and change direction en route from the circuit board 19 to the first and second attachment points 25 and 27. From the first and second locations A and B, the first and second wires 21 and 22 extend circumferentially in the distal end portion 17B of the hollow interior 17 along respective ones of the inner walls 15C and 16C of the case 11, and then radially to the first and second attachment points 25 and 27 (FIG. 7), somewhat like the path of a spiral. A magnet wire that forms a coil 29 component of the transducer component 20 (FIG. 8) includes opposite ends that are connected to the first and second wires 21 and 22. The magnet wire is not included in FIGS. 3, 4, and 7 for illustrative purposes. The magnet wire is shown diagrammatically in FIG. 8, however, with each of the two opposite ends of the magnet wire twisted onto and soldered onto a respective one of the second end portion 21B of the first wire 21 and the second end portion 22B of the second wire 22. In operation, electrical signals produced by the circuit board 19 are coupled to the coil 29 via the first and second wires 21 and 22, and so doing results in the desired electrolarynx sound.

According to a major aspect of the invention, there are provided the two wire-guiding structures 31 and 32, each at a respective one of the first and second locations A and B. The two wire-guiding structures 31 and 32 are similar and so only the first wire-guiding structure 31 is included in the enlarged view of FIG. 9. The first wire-guiding structure 31 has a radially inward facing side 33 that faces toward the central axis of elongation 12, and it defines a radially outward facing first channel 34 that extends along a first channel axis 35. As an idea of size, the first wire-guiding structure 31 has a height 36 of about 0.086 inches, a width 37 of about 0.043 inches, and a length extending along the side 33 perpendicular to the height 36 and the width 37, from a free end 38 of the structure 31 to the inner wall 16C, of about 0.325 inches. In addition, the channel 34 of the wire-guiding structure 31 has a width 39 of about 0.025 inches wide and a depth of about 0.020 inches measured parallel to the width 37. The second wire-guiding structure 32 has a similar size and shape. Of course, those dimensions apply to the illustrated embodiment and they may vary without departing from the broader inventive concepts disclosed.

The first and second wire-guiding structures 31 and 32 are molded integrally with the rest of the plastic first and second sections 15 and 16 of the case 11 so that they have the orientations shown. The inner wall 15C-16C in the distal end portion 17B of the hollow interior is cylindrically shaped and centered on the central axis of elongation 12, and it has, for example, an 0.850-inch inside diameter. Each of the first and second wire-guiding structures 31 and 32 protrudes from the inner wall 15C-16C of the case 11 and extends along a chord of the inner wall, from the inner wall 15C-16C and beyond a respective one of the first and second locations A and B. As illustrated in the enlarged view of FIG. 10, the inwardly facing side 33 of the first wire-guiding structure 31 lies along a first chord 41 of the inner wall 15C-16C, with the first channel 34 facing the inner wall 15C-16C. The first chord 41 is represented by a broken line in FIG. 10 and it subtends and angle of about 75 degrees, with the channel axis 35 being parallel to the first chord 41. The second wire-guiding structure 32 is oriented in a similar manner along a similar chord 42.

As a result of the foregoing, the first and second wire-guiding structures 31 and 32 direct the first and second wires 21 and 22 wire circumferentially as described and illustrated. The first and second wire-guiding structures 31 and 32 maintain bends in the two wires 21 and 22 at the locations A and B so that the wires 21 and 22 bend from longitudinally extending paths coming from the circuit board 19 to circumferentially extending paths heading toward the attachment points 25 and 27, with portions of the wires 21 and 22 preferably being disposed within the channels of those two wire-guiding structures 31 and 32 where they are trapped between the wire-guiding structures 31 and 32 and the inner wall 15C-16C while being held by the wire-guiding structures 31 and 32 from moving longitudinally parallel to the central axis of elongation 12. Although the illustrated wire-guiding structures 31 and 32 define channels, it is within the broader inventive concepts disclosed to have wire-guiding structures that do not define channels in which the first and second wires 21 and 22 are at least partially disposed. It is intended that the broader claims cover such an alternative. Based upon the description and the claims, one of ordinary skill in the art can readily implement an electrolarynx constructed according to the invention, with wire-guiding structures that have any of various shapes and sizes, both with and without channels.

Thus, the invention provides an electrolarynx with features that significantly facilitate fabrication and promote proper functioning. Although an exemplary embodiment has been shown and described, one of ordinary skill in the art may make many changes, modifications, and substitutions without necessarily departing from the spirit and scope of the invention. For example, the transducer component has been described in terms of a known type of electro-mechanical transducer assembly that includes a coil of magnet wire for producing a magnetic field such that it causes a plunger to vibrate against a button-like diaphragm and thereby produce a buzzing electrolarynx sound. Use of a linear motor falls within the broader inventive concepts and the term transducer component herein includes that alternative. As for the other specific terminology used to describe the exemplary embodiment, it is not intended to limit the invention; each specific term is intended to include all technical equivalents that operate in a similar manner to accomplish a similar purpose or function.

What is claimed is:

1. An electrolarynx, comprising:
    a case having an inner wall that defines a hollow interior of the case extending along a central axis of elongation of the case from a mid portion of the case to a distal end portion of the case;
    a circuit board disposed within the mid portion of the case;
    a transducer component disposed within the distal end portion of the case;
    two wires within the case that electrically connect the circuit board to the transducer component, a first one of the two wires extending from the circuit board to a first attachment point on the transducer component, and a second one of the two wires extending from the circuit board to a second attachment point on the transducer component;
    the first wire extending longitudinally within the case from the circuit board to a first location adjacent the inner wall in the distal end portion, and the second wire extending longitudinally within the case from the circuit board to a second location adjacent the inner wall in the distal end portion that is diametrically opposite the first location;
    a first wire-guiding structure at the first location in the distal end portion that functions as means for directing the first wire circumferentially toward the first attachment point; and
    a second wire-guiding structure at the second location in the distal end portion that functions as means for directing the second wire circumferentially toward the second attachment point;
    whereby the first and second wire-guiding structures maintain bends in the two wires from longitudinally extending wire paths coming from the circuit board to circumferentially extending wire paths going to the first and second attachment points on the transducer, thereby facilitating fabrication while avoiding wire interference with transducer operation.

2. An electrolarynx as recited in claim 1, wherein the case comprises a first section that includes the first wire-guiding structure and a second section that includes the second wire-guiding structure, said first and second sections having been assembled together to form the case.

3. An electrolarynx as recited in claim 2, wherein: the first section of the case includes the first wire-guiding structure as an integrally molded part of the first section; and the second section of the case includes the second wire-guiding structure as an integrally molded part of the second section.

4. An electrolarynx as recited in claim 1, wherein:
the inner wall of the distal end portion of the case is circularly shaped in a transverse plane perpendicular to the central axis of elongation; and
the first wire-guiding structure protrudes from the inner wall and extends along a first chord of the inner wall, from the inner wall and beyond the first location.

5. An electrolarynx as recited in claim 4, wherein:
the first wire-guiding structure defines a first channel facing the inner wall; and
the first wire is disposed at least partially within the first channel so that the first wire is directed circumferentially at the first location.

6. An electrolarynx as recited in claim 4, wherein the first wire-guiding structure does not define a channel facing the inner wall in which the first wire is least partially disposed.

7. An electrolarynx as recited in claim 4, wherein the second wire-guiding structure protrudes from the inner wall and extends along a second chord of the inner wall, from the inner wall and beyond the second location.

8. An electrolarynx as recited in claim 7, wherein the second wire-guiding structure defines a second channel facing the inner wall, and the second wire is disposed at least partially within the second channel so that the second wire is directed circumferentially at the first location.

9. An electrolarynx as recited in claim 7, wherein the second wire-guiding structure does not define a channel facing the inner wall in which the first wire is least partially disposed.

10. An electrolarynx as recited in claim 1, wherein:
the first attachment point is diametrically opposite the first location, with the first wire extending circumferentially from the first location and then radially toward the first attachment point; and
the second attachment point is diametrically opposite the second location, with the second wire extending circumferentially from the second location and then radially toward the second attachment point.

11. An electrolarynx as recited in claim 1, wherein:
the first wire includes a second end portion that is attached to the transducer component at the first attachment point with glue;
the second wire includes a second end portion that is attached to the transducer component at the second attachment point with glue; and
the magnet wire includes two free ends that are soldered to respective ones of the second end portion of the first wire and the second end portion of the second wire.

12. An electrolarynx as recited in claim 1, wherein the case comprises:
a first section and a second section that are joined together along a longitudinally extending first joint and a longitudinally extending second joint that is diametrically opposite the first joint, said first section having a first rearward end portion and a first forward end portion, and said second section having a second rearward end portion and a second forward end portion;
a first end cap that is screwed onto the first and second rearward end portions in order to hold the rearward end portions together; and
a second end cap that is screwed onto the first and second forward end portions in order to hold the forward end portions together.

13. An electrolarynx as recited in claim 1, wherein:
the first wire has a first end portion that is connected to the circuit board and a second end portion that is glued to the transducer component at the first attachment point;
the second wire has a first end portion that is connected to the circuit board and a second end portion that is glued to the transducer component at the second attachment point;
the transducer includes a coil of magnet wire having two free ends; and
each of the free ends of the magnet wire is soldered to a respective one of the second end portion of the first wire and the second end portion of the second wire.

\* \* \* \* \*